United States Patent
Redmond et al.

(10) Patent No.: US 11,945,098 B2
(45) Date of Patent: Apr. 2, 2024

(54) FRICTION-BASED TACTILE SENSOR FOR MEASURING GRIP SECURITY

(71) Applicant: Contactile Pty Ltd, Coogee (AU)

(72) Inventors: Stephen James Redmond, South Maroubra (AU); Heba Khamis, Coogee (AU); Benjamin Xia, Castle Hill (AU)

(73) Assignee: CONTACTILE PTY LTD, Coogee (AU)

( * ) Notice: Subject to any disclaimer, the term of this patent is extended or adjusted under 35 U.S.C. 154(b) by 475 days.

(21) Appl. No.: 16/638,882

(22) PCT Filed: Aug. 14, 2018

(86) PCT No.: PCT/AU2018/050859
§ 371 (c)(1),
(2) Date: Feb. 13, 2020

(87) PCT Pub. No.: WO2019/033159
PCT Pub. Date: Feb. 21, 2019

(65) Prior Publication Data
US 2020/0191704 A1    Jun. 18, 2020

(30) Foreign Application Priority Data

Aug. 14, 2017 (AU) .............................. 2017903239
May 24, 2018 (AU) .............................. 2018901816

(51) Int. Cl.
*B25J 13/08*    (2006.01)
*A41D 19/015*    (2006.01)
(Continued)

(52) U.S. Cl.
CPC ...... *B25J 13/083* (2013.01); *A41D 19/01541* (2013.01); *A61B 5/225* (2013.01);
(Continued)

(58) Field of Classification Search
CPC ........ B25J 13/085; B25J 19/02; B25J 13/084; B25J 13/083; B25J 13/082
See application file for complete search history.

(56) References Cited

U.S. PATENT DOCUMENTS 3,895,153 A * 7/1975 Johnston ................... B32B 7/12
                                                        428/494
3,904,234 A * 9/1975 Hill ......................... G01L 1/005
                                                        414/6
(Continued)

FOREIGN PATENT DOCUMENTS

CA         2135463 A  *  5/1996  .............. B25J 19/02
CN       204154423 U     2/2015
(Continued)

OTHER PUBLICATIONS

Espacenet Machine Translation of JP 2005257343 A Which Originally Published On Sep. 22, 2005. (Year: 2005).*
(Continued)

*Primary Examiner* — David A. Rogers
(74) *Attorney, Agent, or Firm* — Dilworth IP, LLC

(57) ABSTRACT

A system for assessing grip security, the system comprising: a contact surface having at least a first contact surface region and a second contact surface region, the first contact surface region being configured to resist slip less than the second contact surface region, a sensor for detecting slip in the first contact region.

20 Claims, 9 Drawing Sheets

(51) Int. Cl.
*A61B 5/22* (2006.01)
*G01L 5/16* (2020.01)
*G01L 5/166* (2020.01)
*G01L 5/22* (2006.01)
*G01N 19/02* (2006.01)

(52) U.S. Cl.
CPC ............... *G01L 5/16* (2013.01); *G01L 5/226* (2013.01); *G01N 19/02* (2013.01); *G01L 5/166* (2013.01)

(56) References Cited

U.S. PATENT DOCUMENTS

| | | | | |
|---|---|---|---|---|
| 4,637,736 | A * | 1/1987 | Andeen | B25J 13/083 |
| | | | | 374/45 |
| 4,766,389 | A * | 8/1988 | Rhoades | B25J 19/02 |
| | | | | 361/283.4 |
| 4,852,928 | A * | 8/1989 | Monforte | B25J 15/04 |
| | | | | 294/902 |
| 6,607,362 | B2 * | 8/2003 | Lum | F04D 13/0666 |
| | | | | 417/423.1 |
| 6,622,575 | B1 * | 9/2003 | Nagata | G06F 3/014 |
| | | | | 73/862.042 |
| 7,857,369 | B2 * | 12/2010 | Chiel | A61B 17/22032 |
| | | | | 606/159 |
| 7,878,075 | B2 * | 2/2011 | Johansson | B25J 13/084 |
| | | | | 73/862.046 |
| 8,029,414 | B2 * | 10/2011 | Ingvast | B25J 9/0006 |
| | | | | 601/40 |
| 8,286,509 | B2 * | 10/2012 | Igarashi | B25J 13/084 |
| | | | | 73/862.627 |
| 8,442,678 | B2 * | 5/2013 | Ichikawa | B25J 9/1612 |
| | | | | 901/33 |
| 8,490,501 | B2 * | 7/2013 | Koyama | B25J 15/0009 |
| | | | | 73/862.381 |
| 8,499,651 | B2 * | 8/2013 | Kishida | G01L 5/228 |
| | | | | 73/862.391 |
| 8,515,579 | B2 * | 8/2013 | Alcazar | B25J 9/1669 |
| | | | | 700/258 |
| 8,800,385 | B2 * | 8/2014 | Ikebe | G01L 5/161 |
| | | | | 73/862.041 |
| 8,882,165 | B2 * | 11/2014 | Lipson | B25J 15/12 |
| | | | | 294/188 |
| 9,120,220 | B2 * | 9/2015 | Bergelin | A61H 1/0288 |
| 9,120,230 | B2 * | 9/2015 | Lipson | B25J 15/12 |
| 9,144,908 | B2 * | 9/2015 | Saen | G01L 5/228 |
| 9,468,847 | B2 * | 10/2016 | Bekri | A63F 13/285 |
| 9,550,298 | B2 * | 1/2017 | Murota | B25J 15/0033 |
| 9,851,271 | B2 * | 12/2017 | Koo | B25J 13/084 |
| 9,878,452 | B2 * | 1/2018 | Davis | A61B 5/6804 |
| 9,914,212 | B2 * | 3/2018 | Wettels | B25J 13/086 |
| 10,040,268 | B2 * | 8/2018 | Sasaki | B32B 3/30 |
| 10,343,290 | B2 * | 7/2019 | Claretti | B25J 15/00 |
| 10,365,172 | B2 * | 7/2019 | Tomita | B25J 13/084 |
| 10,466,784 | B2 * | 11/2019 | Cohen | B25J 13/025 |
| 10,507,584 | B2 * | 12/2019 | Peters | B25J 9/1697 |
| 10,549,429 | B2 * | 2/2020 | Duchaine | G01L 9/0051 |
| 10,576,626 | B2 * | 3/2020 | Rose | B25J 13/08 |
| 10,814,493 | B2 * | 10/2020 | Duchaine | G01L 9/0051 |
| 10,814,494 | B2 * | 10/2020 | Amacker | B25J 13/089 |
| 11,027,436 | B2 * | 6/2021 | Ben | B25J 13/084 |
| 11,077,565 | B2 * | 8/2021 | Lessing | B25J 15/12 |
| 2004/0192130 | A1 * | 9/2004 | Baciu | B32B 27/04 |
| | | | | 442/19 |
| 2007/0227267 | A1 * | 10/2007 | Loeb | B25J 13/084 |
| | | | | 73/862.046 |
| 2008/0202202 | A1 * | 8/2008 | Ueda | G01B 5/012 |
| | | | | 702/41 |
| 2009/0139007 | A1 * | 6/2009 | Bevier | A63B 71/148 |
| | | | | 2/161.1 |
| 2009/0162651 | A1 * | 6/2009 | Rios | A63B 60/08 |
| | | | | 428/419 |
| 2009/0272201 | A1 * | 11/2009 | Loeb | G01L 5/228 |
| | | | | 73/862.041 |
| 2010/0139437 | A1 * | 6/2010 | Ichikawa | B25J 15/0009 |
| | | | | 700/258 |
| 2010/0235145 | A1 | 9/2010 | Ascari et al. | |
| 2012/0240691 | A1 | 9/2012 | Wettels et al. | |
| 2013/0033050 | A1 * | 2/2013 | Matsuoka | B66C 1/42 |
| | | | | 294/86.4 |
| 2013/0261527 | A1 * | 10/2013 | Yick | A61F 13/00987 |
| | | | | 602/53 |
| 2015/0143610 | A1 * | 5/2015 | Pimentel De Oliveira | A41D 19/0058 |
| | | | | 2/167 |
| 2015/0355039 | A1 * | 12/2015 | Duchaine | G06F 3/044 |
| | | | | 428/141 |
| 2018/0015618 | A1 * | 1/2018 | Nadler | B25J 13/082 |
| 2018/0356301 | A1 * | 12/2018 | Tomita | G01L 1/04 |
| 2018/0361596 | A1 * | 12/2018 | Beri | A61H 1/02 |
| 2020/0072691 | A1 * | 3/2020 | Nakayama | G01L 5/165 |
| 2020/0191704 | A1 * | 6/2020 | Redmond | A41D 19/01541 |
| 2021/0031368 | A1 * | 2/2021 | Drumwright | B25J 9/1676 |
| 2021/0041309 | A1 * | 2/2021 | Sun | G01L 1/144 |

FOREIGN PATENT DOCUMENTS

| | | | |
|---|---|---|---|
| CN | 206373923 U | 8/2017 | |
| DE | 10353872 A1 * | 6/2004 | ............. B41F 21/12 |
| DE | 102014221294 A1 | 4/2016 | |
| GB | 2115935 A * | 9/1983 | ............... A61B 5/16 |
| JP | 2000254884 A | 9/2000 | |
| JP | 2005257343 A * | 9/2005 | ............ B25J 13/082 |
| JP | 2005257343 A | 9/2005 | |
| JP | 2007118148 A | 5/2007 | |
| JP | 2009255191 A * | 11/2009 | |
| JP | 2009255191 A | 11/2009 | |
| JP | S6061632 A | 11/2009 | |
| JP | 2017138224 A | 8/2017 | |
| WO | 2010101174 A1 | 9/2012 | |
| WO | 2014045685 A1 | 8/2016 | |

OTHER PUBLICATIONS

Espacenet Machine Translation of JP 2009255191 A Which Originally Published On Nov. 5, 2009. (Year: 2009).*

Sung Joon Kim et al., "Development of a resistive compact slip sensor using dielectric elastomer", Microsystems Technology, Nov. 19, 2016. (Year: 2016).*

Wei Chen et al., "Tactile Sensors for Friction Estimation and Incipient Slip Detection—Toward Dexterous Robotic Manipulation: A Review", IEEE Sensors Journal, Nov. 15, 2018. (Year: 2018).*

International Search Report for Application No. PCT/AU2018/00859 dated Oct. 16, 2018 (4 pages).

International Preliminary Report on Patentabililty for Application No. PCT/AU2018/00859 dated Dec. 6, 2019 (80 pages).

Packard et al., "Utilizing Sensed Incipient Slip Signals for Grasp Force Control," In the proceedings of the 1992 Japan—USA Symposium on Flexible Automation, Jul. 13-15, 1992, San Francisco, CA, 7 pages.

Tremblay et al., "Estimating Friction Using Incipient Slip Sensing During a Manipulation Task," [1993] Proceedings IEEE International Conference on Robotics and Automation, 6 pages.

Son, "Integration of Tactile Sensing and Robot Hand Control," Harvard University, Cambridge Massachusetts, May 1996, 127 pages.

Chen, et al., "Tactile Sensors for Friction Estimation and Incipient Slip Detection—Towards Dexterous Robotic Manipulation: A Review," IEEE Sensors Journal, Sep. 3, 2018, 19 pages.

Heyneman, Barrett et al., Slip classification for dynamic tactile array sensors 11 , International Journal of Robotics Research., vol. 35, No. 4, Mar. 16, 2015 (Mar. 16, 2015) , pp. 404-421.

Marconi L et al., Incipient Slip Detection and Control Using a Rubber-Based Tactile Sensor, 13th Triennal World Congress of IFAC, San Francisco, USA, Jun. 1, 1996 (Jun. 1, 1996), pp. 475-480.

(56) References Cited

OTHER PUBLICATIONS

Keibner A et al., ECIFMBE Proceedings 22: "Multi-tactile sensor concept for the autonomous navigation in human blood vessels", 2009, pp. 1544-1547.

* cited by examiner

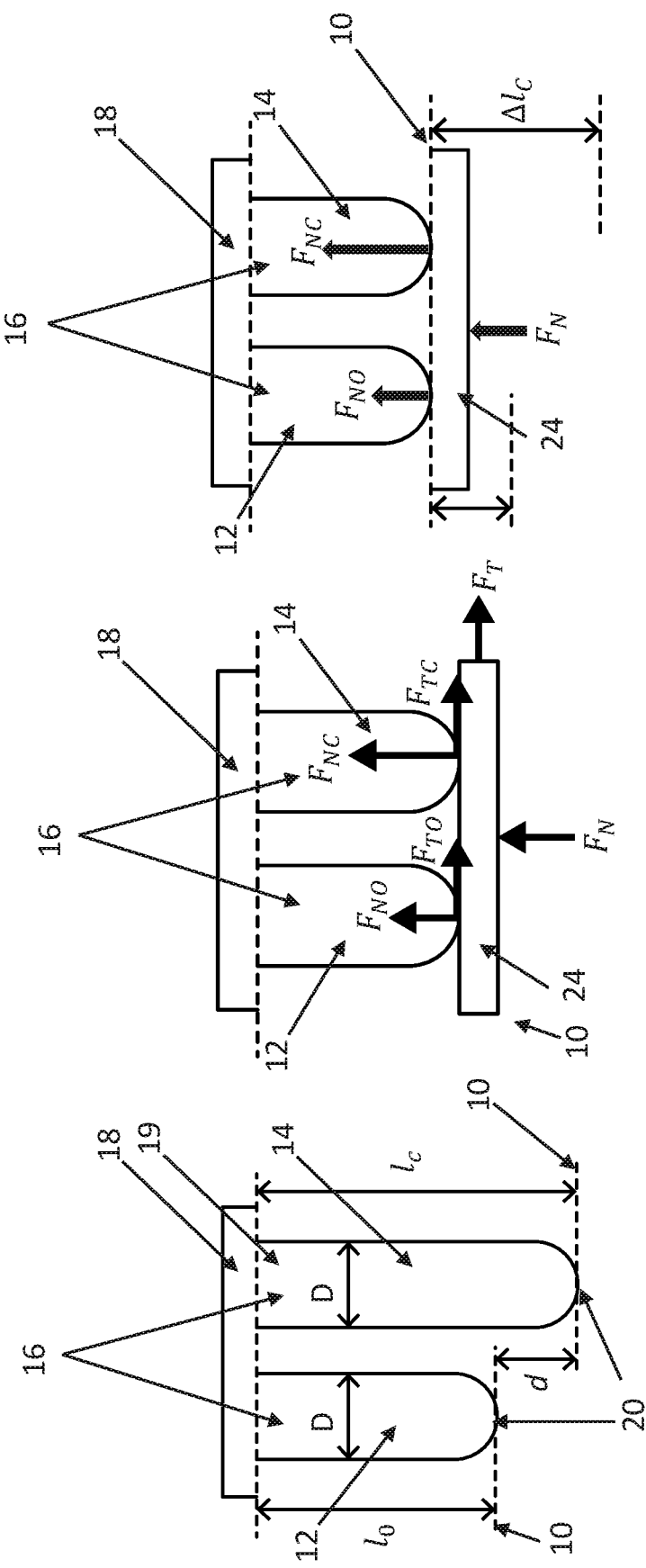

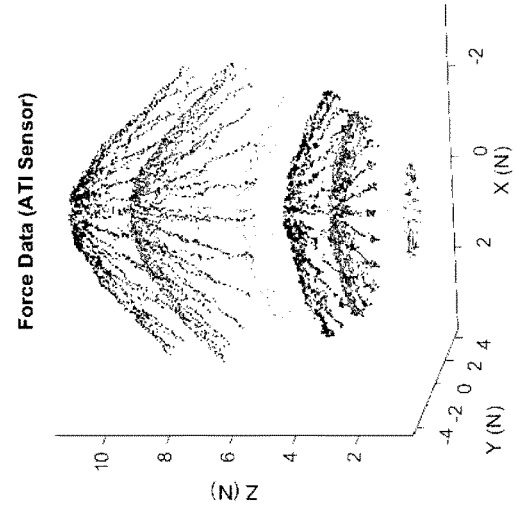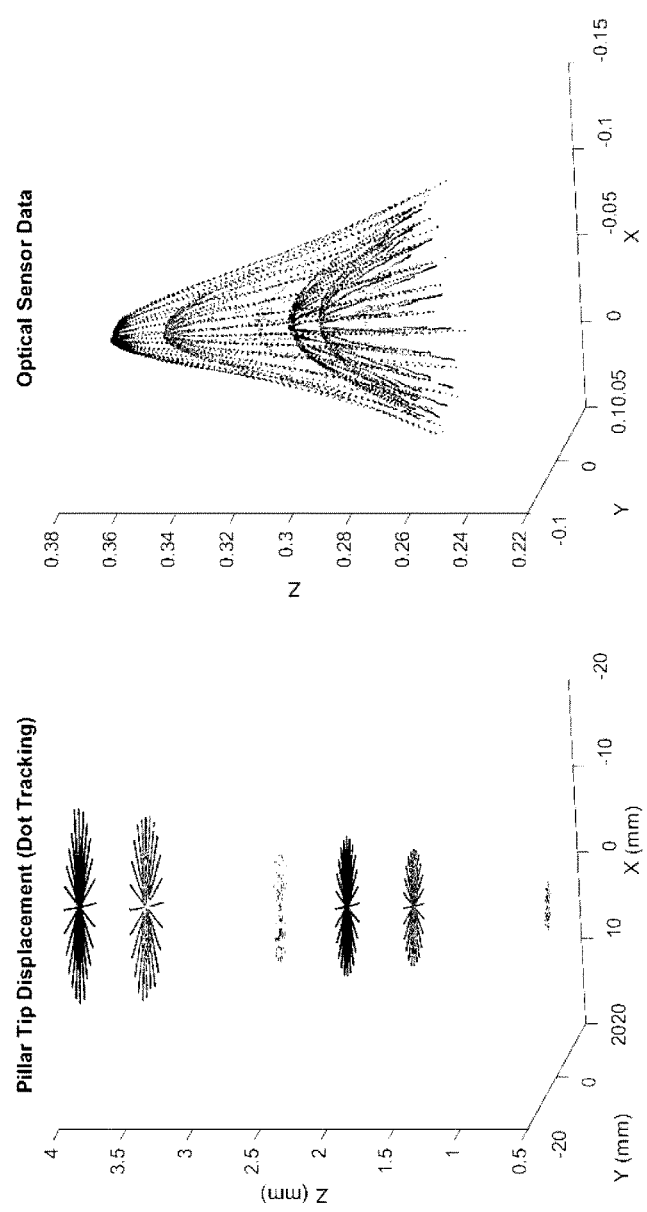
Fig 9A
Fig 9B
Fig 9C

FRICTION-BASED TACTILE SENSOR FOR MEASURING GRIP SECURITY

TECHNICAL FIELD

This disclosure relates to devices and methods for measuring grip security and devices and methods for improving grip security.

BACKGROUND ART

Grasping and lifting objects using robotic grippers is a difficult task. Robotic grippers do not have the human hand's ability to detect valuable information about the object and the contact interface. In most cases grippers do not have any tactile feedback. Those which do have tactile feedback typically measure one feature, for example grip forces, or detect the object sliding from the grasp. Although robotic and prosthetic gripper design continues to evolve, trying to emulate the dexterity of the human hand, it is still far from achieving comparable performance.

The field of tactile sensing is an active one and aims to fill this gap; however, the majority of existing tactile sensors focus on determining the normal and tangential forces at the interface. While these quantities are important, there are certainly other tactile parameters that are also important for dexterous manipulation. Two such parameters are the coefficient of static friction (s) and the occurrence and extent of incipient slip.

The coefficient of static friction of the contact interface helps to determine the minimum grip (normal) force required to hold an object of a specific weight (tangential force). In certain grip poses, if the coefficient of static friction is accurately estimated and the tangential force can be measured, then the grip (normal) force can be adjusted to securely hold the object.

A number of tactile sensors have been reported in the literature for measuring the coefficient of static friction and the occurrence and extent of incipient slip, however, many of these sensors suffer from one or more of the following limitations:
 (i) the need to explore the object prior to attempting to grip it,
 (ii) the occurrence of a gross slip during manipulation prior to obtaining a measurement of coefficient of static friction,
 (iii) the inability to provide a continuous measurement of the coefficient of static friction in the case of changing frictional conditions, and
 (iv) the need to continuously monitor normal and tangential forces.

Some of these problems may be solved or mitigated or at least an alternative may be provided within the present disclosure.

An alternative to measuring the coefficient of static friction is to detect incipient slip, and adjust the grip force following the occurrence of such an event. Incipient slip is defined as a relative displacement taking place on a localised region of the contact interface, while total slip involves a relative displacement across the whole contact interface. However, at the present time, there is still no dominant, well-established technology for artificially sensing slip, despite the multitude of slip sensors reported in the literature.

It would therefore be advantageous to the art if a device were capable of accurately detecting incipient slip while the grip is still secured, thereby enabling force modulation before total loss of grip is experienced.

MIT researchers have developed a device to detect incipient slip called GelSight. It utilises a transparent silicone and camera to measure slip on the contact area by tracking the movement of a dot pattern tattooed onto the silicone. However, it is limited in its ability to detect incipient slip as it uses a flat and contiguous surface. The flat surface limits the establishment of a pressure differential, and hence differential traction, across the contact interface. The contiguous nature of the elastomer sensing material discourages independence of movement between different localised regions of the sensing interface, which further discourages the occurrence of incipient slip. The GelSight sensor is also limited to sensing relatively low-frequency tactile events, as it relies up image processing of a video stream in order to detect movement of the silicone at the contact interface.

It would be additionally advantageous to the existing art, were a tactile sensor device capable of reliably detecting and signalling impending slip while simultaneously estimating friction, irrespective of the material it was in contact with.

It is to be understood that, if any prior art is referred to herein, such reference does not constitute an admission that the prior art forms a part of the common general knowledge in the art, in Australia or any other country.

SUMMARY

Disclosed is a system for assessing grip security, the system comprising a contact surface having at least a first contact surface region and a second contact surface region, the first contact surface region being configured to resist slip less than the second contact surface region. The disclosed system further comprises a sensor for detecting slip in the first contact region. In some forms the contact surface is deformable.

The detection of slip can be utilised to assess grip security and to supply feedback within the system such that the grip strength is increased to increase grip security.

In some forms, the contact surface comprises a plurality of protrusions extending from a base surface. In some forms the protrusions are compressible. In some forms the protrusions are in the form of elongate pillars. The protrusions in the first contact region may in some embodiments extend away from the base surface a distance less than the protrusions in the second contact region. In some embodiments the protrusions may be positioned to form an array. Also disclosed is a method for assessing grip security, the method comprising detecting slip at a contact surface, wherein the contact surface has at least a first contact surface region and a second contact surface region, the first contact surface region being configured to resist slip less than the second contact surface region. In some forms the method comprises utilising a sensor.

The variance in protrusion height or distance from the base surface may be advantageous as in some forms of use it enables the device to detect incipient slip. The difference in protrusion heights causes protrusions to experience a normal force dependent upon the distance the protrusion extends from the base surface when the protrusions are compressed to the same final height. When a tangential force is also applied, under the assumption that the protrusions do not bend appreciably, then all of the protrusions having the same cross-sectional area experience the same tangential force. Consequently, the ratio of tangential force to normal force experienced by each protrusion varies with the difference in protrusion heights. If it is further assumed that the surface of the sensor holds a constant coefficient of static friction, when the tangential force increases, the protrusion under the lowest normal force (i.e., the shortest protrusion when the device is unloaded) will slip first when the tangential-to-normal force ratio is greater than the coefficient of static friction. As the tangential force increases further, the next shortest protrusion will slip, and so on, until the tallest protrusion has slipped. In this way, each incipient slip event acts as a warning that the grip/normal force should be increased to maintain the stable grip of an object.

In a further embodiment of the disclosure, the movement of individual protrusions may be independent of one another. The independent movement of at least two pillars is advantageous in that it enables the measurement of the relative movement on the contact surface which may occur only at differing levels across the contact surface.

In a further embodiment of the disclosure, the uncompressed height from the base surface of a protrusion in the first contact region is shorter than that of a protrusion in the second contact region.

In a further embodiment of the disclosure, the normal force experienced by a protrusion in the first contact region is less than that of a protrusion in the second contact region.

In a further embodiment of the disclosure, the protrusions are pillars.

In a further embodiment of the disclosure, a first end of a protrusion is connected to the base surface, and a second opposing end of the protrusion forms a rounded or spherical or otherwise non-flat tip.

In a further embodiment of the disclosure, the contact surface is fabricated primarily from silicone.

In some embodiments of the disclosure the base surface may be planar, while in other embodiments the base surface may be non-planar. When the surface of the object being grasped is planar the relative compression of each protrusion can easily be determined against a common base surface, even if the base surface is not planar. The forces in three dimensions can be measured regardless of the surface shape or whether the base surface is non-planar.

The system further comprises a sensor, or sensor system, adapted to measure the slip at the first contact region to detect incipient slip. The sensor may be in various forms.

In some forms a sensor is positioned behind the base surface at a location adjacent each cavity.

In some forms the sensor is adapted to detect incipient slip.

In some forms the sensor is adapted to estimate friction.

In some forms an aperture having a smaller diameter than the cavity is located between the sensor and the cavity.

In some forms the sensor comprises a quadrant photodiode configured to detect light emanating from LEDs positioned on a cavity side of the base surface within a given protrusion, reflecting from a reflector located at or near the distal end of the cavity and travelling through the aperture to the sensor.

In some forms the contact surface comprises a plurality of protrusions extending from a base surface, the protrusions having an internal cavity, and wherein the sensor comprises a CCD array, the system being configured such that the CCD array detects light emanating from the base surface into the cavity, reflecting from a reflector located at the distal end of the cavity, and travelling through an aperture in the base surface to the sensor.

In some forms, compression of the protrusions in the z-axis normal to the base surface results in expansion of the diameter of the detected light spot.

In some forms the contact surface comprises a plurality of protrusions extending from a base surface, the protrusions having an internal cavity, and wherein the sensor comprises a CMOS light-sensitive array, the system being configured such that the CMOS light-sensitive array detects light emanating from the base surface into the cavity, reflecting from a reflector located at the distal end of the cavity, and travelling through an aperture in the base surface to the sensor.

In some embodiments of the disclosure, the rate at which incipient slip warnings are signalled by the sensor, the rate at which slip events are detected, or a number of warnings, may be used to indicate a level of urgency with which a corrective action is required, or the magnitude of force required for a corrective action.

In some forms, disclosed is a method of estimating friction at a contact surface, the method comprising providing a plurality of protrusions extending from a base surface to a tip, measuring displacement of the tip in three spatial dimensions, estimating forces applied to the tip in three spatial dimensions.

In some forms, the system detects slip when one or more protrusions no longer move at the same speed as other protrusions in the array. In some forms the system detects slip through vibration. In some forms, after detection of slip, the system reviews the ratio of tangential to normal force at the moment of slip to allow an estimate of the coefficient of friction.

In some forms, disclosed is a method of detecting torque normal to a contact surface, the method comprising providing a plurality of protrusions extending from a base surface to a tip, measuring displacement of the tip in three dimensions, estimating forces applied to the tip in three dimensions, measuring deflection around a normal axis to the base surface at the point at which the protrusion extends.

In some forms, disclosed is a method of analysing slip movement or texture at a contact surface, the method comprising providing a plurality of protrusions extending along an axis from a base surface to a tip, measuring displacement of the tip in three dimensions at a high resolution such that vibration of the tip is measured, utilising the measurement of vibration to estimate texture or detect slip.

BRIEF DESCRIPTION OF THE DRAWINGS

Embodiments will now be described by way of example only, with reference to the accompanying drawings in which FIG. 1A is a cross-sectional view of an embodiment of a contact surface of the disclosure;

FIG. 1B is a cross-sectional view of the embodiment of FIG. 1 in a compressed condition;

FIG. 1C is a cross-sectional view of the embodiment of FIG. 1 in a compressed condition;

FIG. 8A shows the high friction surface, FIG. 8B shows the base friction surface and FIG. 8C shows the low friction surface;

FIGS. 9A-9C provide a graphical representation of detection of displacement and force using one embodiment of the disclosure. FIG. 9A provides a reference pillar tip displacement, FIG. 9C provides a reference force data and FIG. 9B shows the optical sensor data output;

DETAILED DESCRIPTION

Figure 3:
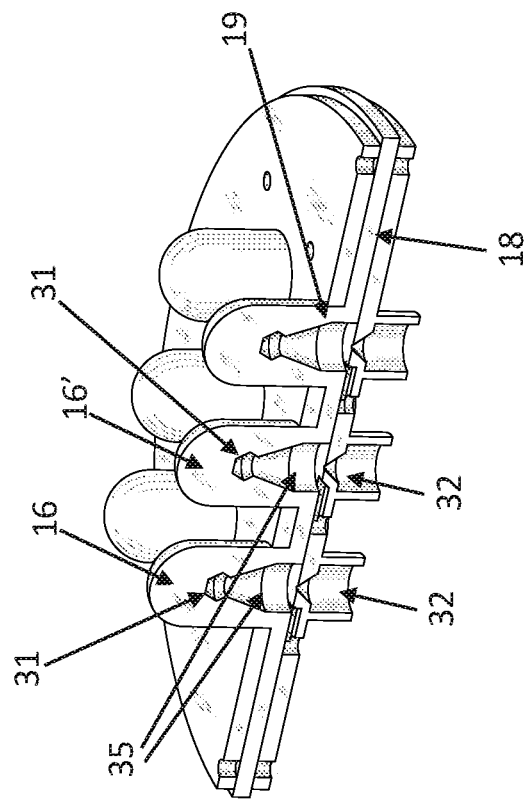
FIG. 3 is a perspective cross-sectional view of a contact surface of the disclosure.

In the following detailed description, reference is made to accompanying drawings which form a part of the detailed description. The illustrative embodiments described in the detailed description, depicted in the drawings and defined in the claims, are not intended to be limiting. Other embodiments may be utilised and other changes may be made without departing from the spirit or scope of the subject matter presented. It will be readily understood that the aspects of the present disclosure, as generally described herein and illustrated in the drawings can be arranged, substituted, combined, separated and designed in a wide variety of different configurations, all of which are contemplated in this disclosure.

In FIG. 1, disclosed is a system for assessing grip security, the system comprising a contact surface 10 having at least a first contact surface region 12 and a second contact surface region 14. In the illustrated form, the contact surface is in the form of a plurality of protrusions 16 extending from a base surface. In FIG. 1 only two protrusions 16 are shown, however it will be clear to the person skilled in the art that the contact surface may comprise a plurality of protrusions 16 extending from the base surface 18. The protrusions 16 are in the form of elongate pillars having an attachment end 19 engaged with or integral with the base surface 18 and extending to a tip 20 having, in some embodiments, a hemispherical end profile. In the illustrated form the elongate pillars have similar cross-sectional dimensions and different lengths of extension from the base surface. In this illustrated form, the variation in distance the protrusion extends from the base surface defines the first contact surface region 12 and the second contact surface region 14. Specifically, the first contact surface region is configured to resist slip less than the second contact surface region. In the illustrated form, only two elongated protrusions are shown, having different heights relative to one another.

FIG. 1 is a simplified model of a possible embodiment, whereby a longer central protrusion or pillar, with height $l_C$, is surrounded by eight shorter outer pillars, each with height $l_O$. Alternative embodiments include multiple pillars of varying heights.

FIG. 1A illustrates two protrusions 16 when uncompressed, each protrusion being in the form of a pillar and having equal diameters, D, but different heights, $l_C$ and $l_O$.

In FIG. 1B, the device 10 is illustrated in contact with a flat surface 24 such as the surface of an object which is being grasped. In this figure, both pillars are compressed by a gross normal force $F_N$ to the same final height, resulting in a different normal (compression) force on each pillar.

FIG. 1C illustrates the addition of a tangential force that acts by shearing the flat surface 24 that the sensor is in contact with, with each of the protrusions 16 also thereby experiencing a tangential force. When no protrusions are slipping against the surface, and assuming that the pillars cannot bend appreciably, they all experience the same tangential force, and the sum of the tangential forces is equal to the gross tangential force, $F_T$.

In some embodiments of the disclosure, the movement of individual protrusions 16 may be independent of one another. The independent or partially independent movement of at least two protrusions in the form of pillars 16 is advantageous in that it enables the measurement of the relative movement on the contact surface which may occur only at differing levels across the contact surface 10.

In some embodiments of the disclosure, the contact surface 10 is fabricated primarily from silicone.

As shown in FIG. 1C, the protrusions 16 of the first surface contact area 12 are under a smaller normal force than is the longer protrusion 16' of the second surface contact area 14. In some forms, the assumption is made that the coefficient of static friction is the same for each protrusion; the outer protrusions of the first contact surface region 12 of the embodiment shown in FIG. 2 will slip at a smaller gross tangential force than the central protrusion 16' of the second contact surface region.

If the spring constant (k) and diameter (D) of a single protrusion are known, and the tangential and normal force are measured at the moment of slip of the shorter protrusions, then it is possible to predict the ratio of gross tangential to normal force at which the longer protrusion will slip. The coefficient of static friction is thus an estimation of the ratio of the tangential force to normal force at the moment of slip for the longer protrusion. In some forms the gross force across the device is measured and apportioned to the protrusions, assuming the material is linear elastic. In some not illustrated forms the force can be individually detected for protrusions or groups of protrusions.

Ideally, since the protrusion is not slipping, it should be deflecting at the same velocity as the surface against which it is compressed. By contrast, when the protrusion slips, the deflection velocity should trend towards 0 mm/s. In practice, due to bending of the protrusion or pillar, the moment of slip was determined as the moment when the deflection velocity of a shorter protrusion decreases to 20% of the deflection velocity of the longest protrusion, conditional on the deflection velocity of the longest protrusion being sufficiently large.

With more protrusions and more height differences, a larger range of frictions and normal forces may be accommodated for, and more warnings are possible to prevent loss of the object as the tangential force increases. The rate at which warnings are signalled, as well as the number of warnings, could indicate the urgency with which corrective action is required. Furthermore, with each warning, more information about the contact interface can be known.

Both with and without continuous normal and tangential force monitoring, the disclosed device can advantageously be used to improve dexterous manipulation in robotic and prosthetic grippers. Without continuous monitoring, the rate at which warnings are signalled, as well as the number of warnings, could still indicate the urgency with which corrective action is required as well as the magnitude of the corrective action. With continuous force monitoring, it may be possible to also determine the coefficient of static friction, and grip corrections would be more informed. Regardless of the type of monitoring, it is possible for a warning to be issued when incipient slip is detected.

In some embodiments of the device, the contact surface 12 is planar such that the relative compression of each protrusion can be determined.

The system in some forms further comprises a sensor, or sensor system, adapted to measure the slip at the first contact region 12 to detect incipient slip. The sensor may be in various forms.

Figure 2:
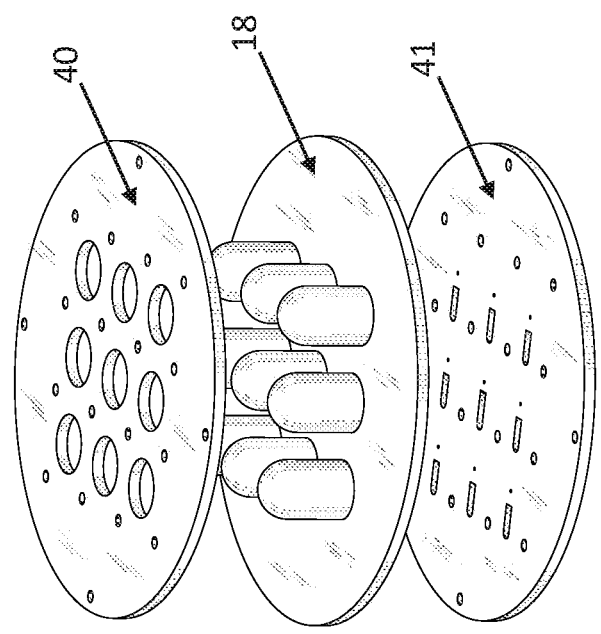
FIG. 2 is a perspective view of a contact surface of the disclosure.

As shown in FIG. 2, the contact surface may comprise a base surface 18 with a plurality of protrusions extending therefrom. In some forms the contact surface further comprises a lower support surface 41 and an upper support surface 40. In some forms the upper support surface includes a plurality of apertures through which the protrusions may extend. In some forms the lower surface 41 may include support or cavities for supporting sensors or other system parts.

Figure 4:
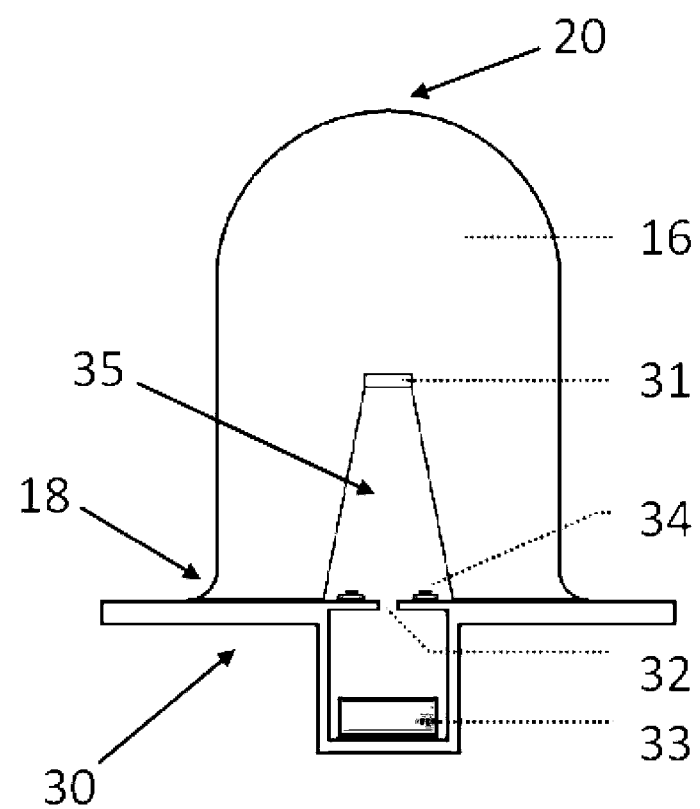
FIG. 4 is a cross-sectional view of an embodiment of the contact surface integrated with a sensor system as per the disclosure.

In some embodiments of the device, such as is illustrated in FIGS. 3 and 4, an illuminated reflector 31, aperture 32 and light sensor 33 form a pinhole camera configuration 30, allowing the three-dimensional deflection of the illuminated reflector 31 to be measured. This deflection correlates with the three-dimensional deflection of the tip of the protrusion 16. A pinhole camera configuration 30 is one where light from a source 34 passing through an aperture 32 projects an inverted image of the source onto a screen or sensor 33 below. The light source 34 is shone up a cavity 35 inside each protrusion 16 so as to reflect off a reflector 31 at the distal end of the cavity 35, and back through the pinhole aperture 32 onto a sensor 33 mounted some appropriate distance from the pinhole aperture 32, behind the base surface 18.

In some embodiments of the device, the light source 34 originates from a small circular disk, wherein a circular light spot will be projected. By monitoring the position of the light spot, the sensor 33 is able to detect the three-dimensional position of the source 34 relative to the aperture 32. In some embodiments the light spot enlarges when the protrusion is compressed meaning deformation along an axis normal to the base can be measured.

The device further allows measurement of change or deformation in three dimensions, that is, in the x and y axis of a tangent plane of the base surface and the z axis which extends normal to the base surface at the point a given protrusion extends from the surface.

Visual representation of change or deformation in all three axes allows the three-dimensional displacement applied to the protrusion or the tip of the protrusion to be measured. This three-dimensional visual representation of displacement comprises visual representations of the movement of the light spot to demonstrate angular movement of the protrusion in the x-y plane tangential to the base surface and visual representation of movement in the z-axis normal to the base surface through a change in the size of the light spot. This visual representation allows forces applied to the protrusion to be determined in all three dimensions. This measurement of three-dimensional force also allows estimation of friction when slippage occurs.

In some forms, the system detects slip when one or more protrusions no longer move at the same speed as other protrusions in the array. In some forms the system detects slip through vibration. In some forms, after detection of slip, the system reviews the ratio of tangential to normal force at the moment of slip to allow an estimate of the coefficient of friction.

Moreover, measurement of forces in three dimensions allows the array of protrusions to estimate torque because the x-y deflection or curl of force around the z axis can be sensed. This estimation of torque allows for increased grip security as the grip force can be increased to account for increasing torque as appropriate.

Measurement of three-dimensional displacement with a high bandwidth and very high spatial resolution allows sensing of vibration in the protrusions. Sensing vibration provides an alert relating to slip events. Alternatively, sensing vibration provides a means of sensing texture and an ability to distinguish between textures. Additionally, the sensing of vibration may lead to transduction of voice or music or other sound from a vibrating surface.

In some embodiments of the device, a cavity 35 inside the protrusion may contain a reflector disk 31 lit by LEDs 34 and the aperture 32.

In some embodiments of the device, the cavity 35 has a conical shape.

In some embodiments of the device, a sensor 33 in the form of a quadrant photodiode that sits below the aperture 32 may detect the position and/or size of the projected light spot relayed from the reflector 31. In such an embodiment, calculation of the light spot position correlates with the position of the tip of the protrusion in the x-y plane tangential to the base surface. This calculation uses a relatively simple formula whereby each axis is calculated by subtracting the difference between sensor halves and normalizing against the total received light. Similarly, the light spot size correlates with the position of the tip of the protrusion along the z-axis normal to the base surface which correlates with compression or release along the z-axis normal to the base surface. Calculation of the position of the tip along the z-axis can be simply calculated by measuring the intensity of light falling on the photodiodes. The simplicity of these calculation makes the design suitable for a microprocessor, even with large arrays of sensors.

In some embodiments of the device, a pinhole camera configuration 30 is capable of measuring the direction and magnitude of protrusion 16 deflection in two dimensions by examining the relative proportions of light illuminating each of the four quadrants of the photodiode sensor 33; as the protrusion 16 deflects the direction of the light beam shining through the pinhole aperture 32 will change. For smaller scale embodiments of the device, the photodiode sensor 33 could be replaced with a CCD or CMOS light-sensitive array. Variations and modifications may be made to the parts previously described without departing from the spirit or ambit of the disclosure.

EXAMPLES

In some illustrated embodiments, estimating forces on the protrusions or pillars may be performed as follows. It is assumed that the material behaves as a linear elastic according to Hooke's Law. It is noted that the gross normal force $F_N$ is the sum of the normal forces acting on each pillar.

In the case of a single central pillar, surrounded by eight outer pillars, this means:

$$F_{NC} = k\Delta l_C, \tag{1a}$$

$$F_{NO} = k\Delta l_O = k(\Delta l_C - d) = F_{NC} - kd, \text{ and} \tag{1b}$$

$$F_N = F_{NC} + 8F_{NO} = 9k\Delta l_C - 8kd, \tag{1c}$$

where k is the spring constant of the elastic material of the pillars. Therefore:

$$F_{NC} = \frac{F_N}{9} + \frac{8kd}{9}, \text{ and} \quad (2a)$$

$$F_{NO} = \frac{F_N}{9} - \frac{kd}{9}. \quad (2b)$$

When a tangential force is also applied to the sensor by shearing the surface that is in contact, each of the pillars also experiences a tangential force (see FIG. 1C). When all pillars are stuck to the surface (not slipping), and assuming that (i) the compressive strain on the pillars is small relative to their height, (ii) the difference in height between the longer and shorter pillars is also small relative to height, and (iii) the pillars do not bend appreciably relative to their height, then they all experience approximately the same tangential force, and the sum of these tangential forces is equal to the gross tangential force, $F_T$. In the case of a single central pillar, surrounded by eight outer pillars, this means:

$$F_{TC} = F_{TO}, \text{ and} \quad (3a)$$

$$F_T = F_{TC} + 8F_{TO} = 9F_{TO}, \quad (3b)$$

where $F_{TC}$ is the tangential force on the central pillar and $F_{TO}$ is the tangential force on one of the outer pillars.

Because the outer pillars are under a smaller normal force, and $\mu_s$ is the same for each pillar, the outer pillars will slip at a smaller gross tangential force than the central pillar. The outer pillars will start to slip when:

$$F_{TO} > \mu_s F_{NO}. \quad (4)$$

This occurs when the gross tangential force is:

$$F_T^{sO} = 9F_{TO} > 9\mu_s F_{NO} = 9\mu_s \left( \frac{F_N^{SO}}{9} - \frac{kd}{9} \right) = \mu_s (F_N^{SO} - kd). \quad (5)$$

While the outer pillars are slipping and the central pillar is still stuck, the outer pillars are contributing a limited amount of tangential force to the gross tangential force, due to the coefficient of kinetic friction ($\mu_k$):

$$F_{TO} = \mu_k F_{NO}, \quad (6a)$$

and the central pillar will start to slip when:

$$F_{TC} > \mu_s F_{NC}. \quad (6b)$$

This occurs when the gross tangential force is:

$$F_T^{sC} = \quad (7)$$
$$F_{TC} + 8F_{TO} > \mu_s F_{NC} + 8\mu_k F_{NO} = \frac{\mu_s}{9}(F_N^{sC} + 8kd) + \frac{8\mu_k}{9}(F_N^{sC} - kd).$$

Now, $\mu_s$ is always greater than or equal to $\mu_k$, however, if it is assumed that $\mu_s = \mu_k$, then Eq. (7) can be simplified to:

$$F_T^{sC} = \mu_s F_N^{sC}. \quad (8)$$

Combining equation (5) and (8) gives:

$$\mu_s = F_T^{sC}/F_N^{sC} = F_T^{sO}/(F_N^{sO} - kd), \quad (9)$$

meaning, if k and d are known, and the gross tangential and normal force are measured at the moment of slip of the outer pillars ($F_T^{sO}$ and $F_N^{sO}$, respectively), it is possible to predict the ratio of gross tangential-to-normal force at which the central pillar will slip; that is, it is possible to estimate the coefficient of static friction by sensing when the outer pillars slip and then examining the forces at that time.

In some forms the diameter of the base of the sensor (from which the pillars emanate) Dtotal=80 mm with a thickness of 3 mm, and each of the cylindrical pillars had a diameter of D=10 mm and a hemispherical ending, with approximately 15 mm centre to centre spacing. Hemispherical ends were chosen, as flat ends with sharp edges would cause large compressive forces to grow on the edge of the pillar contact area before it would slip. In this embodiment of the sensor (as with the simple model above), eight outer pillars surround a single central pillar, in a 3×3 grid arrangement. The height of the central pillar was $l_C$=15 mm, and the height of outer pillars was $l_O$=14 mm; i.e., the height difference between the central pillar and the outer pillars is d=1 mm. To fabricate this prototype, silicone was cast into a 3D printed ABS plastic mould.

Figure 5:
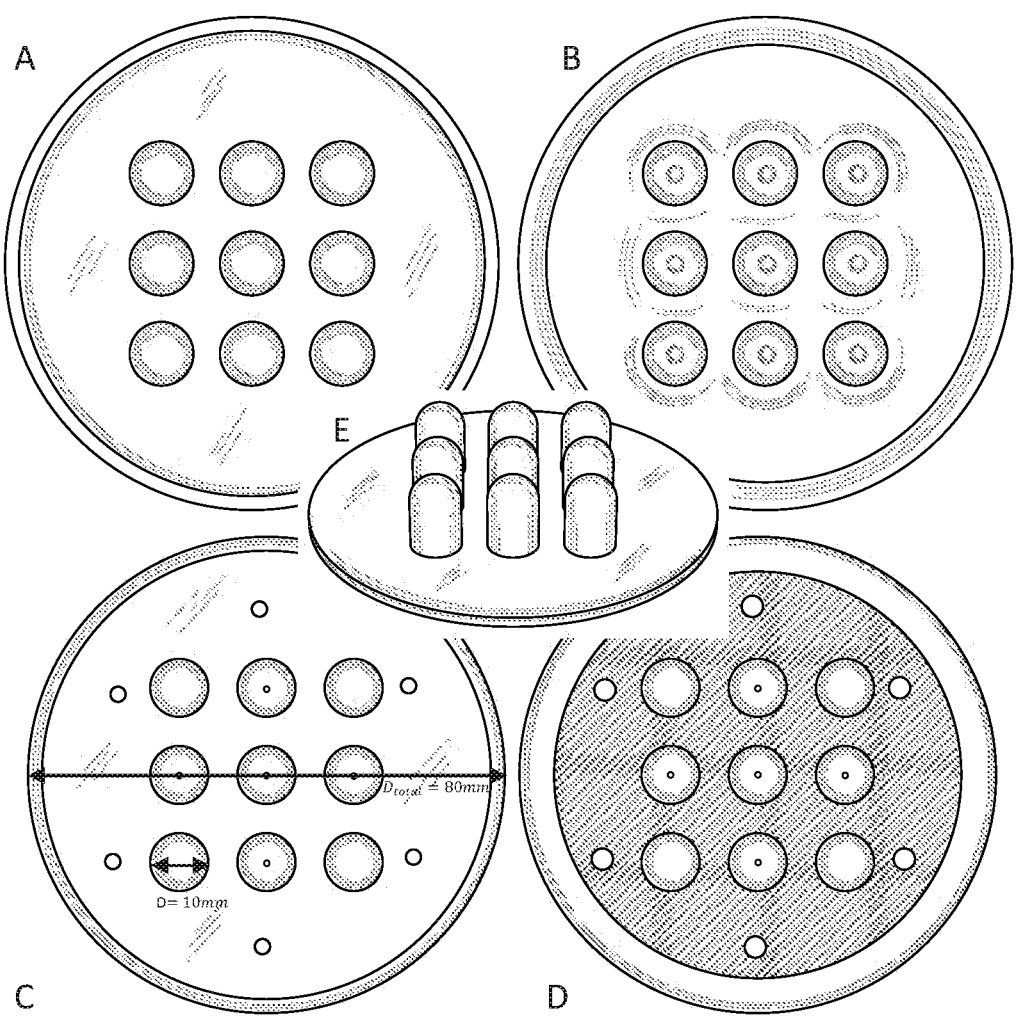
FIG. 5 shows fabrication of a prototype of one embodiment of the disclosure, showing both mould and resultant silicon profile.

The mould was printed in thermoplastic using a 3D Printer. To smooth the 3D print lines on the surface of the mould, it was suspended over an acetone vapour bath for 3 hours at room temperature. FIGS. 5A and 5B show the mould before and after the acetone vapour bath, respectively.

A two-component, skin-safe silicone with low viscosity for easy flowing, and short curing period was used as the material for the prototype. The two components were mixed in equal parts as per the manufacturer instructions and the casting was performed in a single pouring. Degassing procedures were not required, however the silicone was poured from a height to allow better control of the pouring stream, and the mould was shaken gently to remove any bubbles present in the silicone. The silicone was de-moulded after curing (see FIG. 5C-5E). FIG. 5C shows a silicone prototype, top view; FIG. 5D shows the prototype with mounting support; FIG. 5E shows the silicone prototype, side view.

To validate the operation of the prototype, a number of experiments were performed to apply normal and tangential forces to the prototype. To perform these test procedures, a test rig was used, comprising of an XYZ-stage, a 3D force/torque sensor, the prototype, a transparent acrylic surface, and a camera. The test rig and test procedures are described below.

Figure 6:
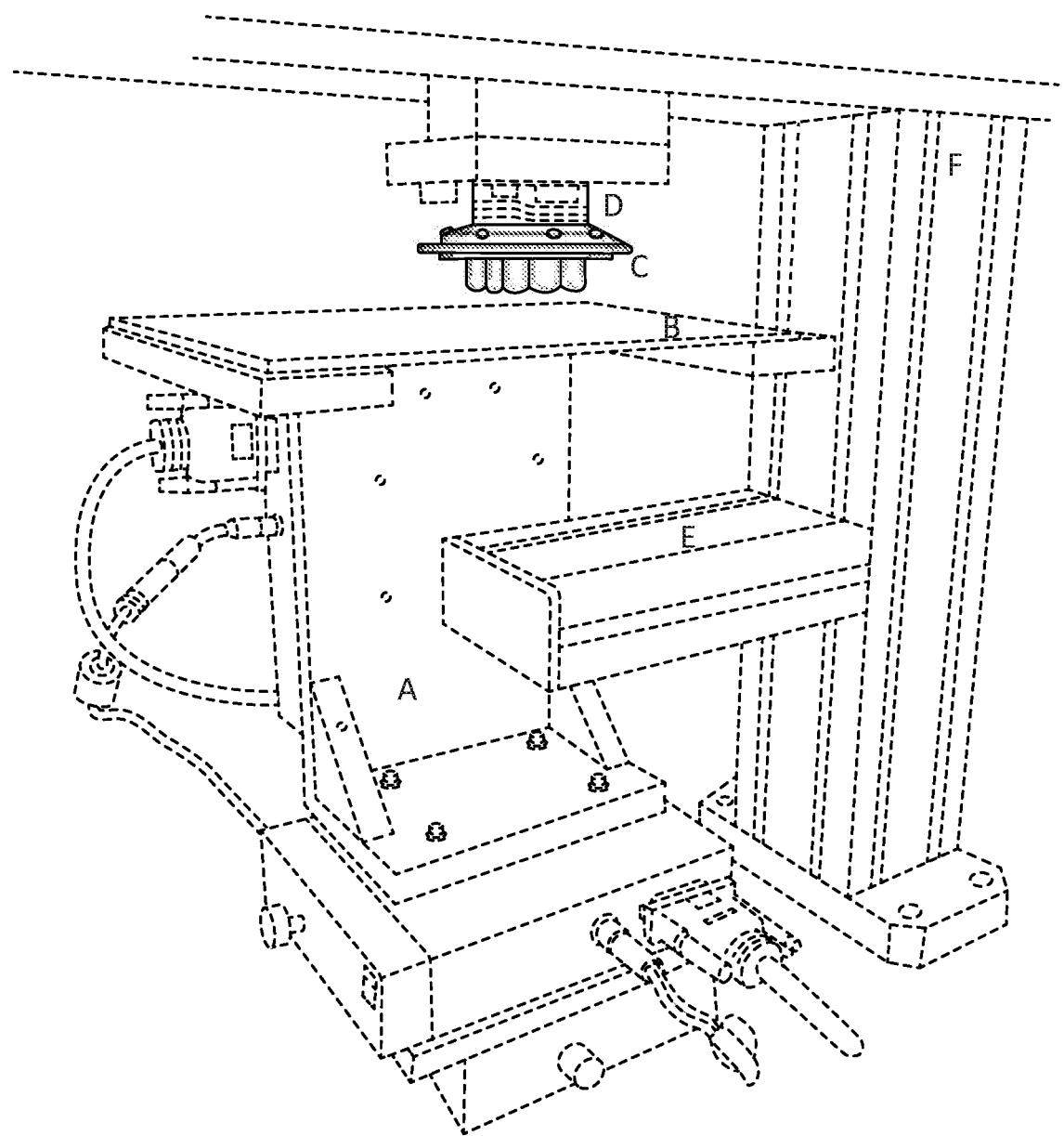
FIG. 6 shows a test rig for testing at least one embodiment of the disclosure.

FIG. 6 shows an exemplary test rig for testing a prototype of at least one embodiment of the disclosure. The figure shows XYZ-stage labelled A, acrylic surface labelled B, prototype labelled C, 3D force/torque sensor labelled D, platform for video capture labelled E, and support frame labelled F.

The XYZ-stage shown in FIG. 6 consisting of three translation stages (M-605.1DD, Physik Instrumente (PI) GmbH & Co. KG, Karlsruhe, Germany) was used to bring a transparent acrylic surface into contact with the prototype and then shear the acrylic surface across the surface of the prototype. Each of the stages have a travel range of 25 mm with a maximum velocity of 50 mm·s$^{-1}$, and accuracy of 0.1 μm with step sizes down to 0.3 μm. Compressing produces a normal force acting on the pillars and shearing of the surface while in contact with the object to be gripped produces tangential forces on each of the pillars.

A 3D force/torque sensor (Mini40, SI-80-4, ATI Industrial Automation, Apex, N.C., USA) was mounted between the prototype and a support frame (see FIG. 6D). The forces and torques acting on the prototype were sampled at 1 kHz with a PowerLab 16/35 data acquisition unit (AD Instruments, Bella Vista, NSW, Australia).

Video of the prototype in contact with the transparent acrylic surface was captured with the native video recording app of a 16 GB iPhone 6 (model A1586). The iPhone was placed on a platform such that the pillars are viewed through the transparent acrylic surface from (approximately 100 mm) directly below with the center pillar positioned in the middle of the image. The iPhone was connected to a MacBook Pro running QuickTime Player 10.4 to record the iPhone screen in .MOV format with 1334×750 pixel resolution at 59.97 fps (frames·s$^{-1}$). Camera calibration was performed using the MATLAB (R2014b, Mathworks, Natick, Mass., USA) Camera Calibration App. The lens distortion coefficients (radial and tangential) were calculated and at the edges of the sensor (beyond the maximum deflection of any of the pillars) the distortion was no greater than 1.1 pixels, which corresponds to approximately 0.12 mm. By comparison, the tracking dots on the pillars measure approximately 5 pixels in diameter. Since this distortion has the effect of biasing the measurement of pillar deflection, the effect on the results is only to change the time point at which the pillars are determined to have slipped relative to the stage; however, determining this event time is much more dependent on the slip detection rule used.

A small hole was created with a pin at the central point of the selected pillars, which was filled with black ink to form a reliable marker for tracking during video analysis. Furthermore, a black and white checkerboard pattern comprising of a row of three 10 mm squares was attached to the acrylic surface to provide a reference point for tracking the position of the surface as well as to provide a reference for the spatial unit conversion (pixels to mm) which was reasonable due to the negligible lens distortion.

The XYZ-stage is programmed to move vertically towards the prototype to a predetermined position that results in the desired normal force (0.5 N for measuring µs, and 5, 7.5, 10, 12.5 and 15 N for analysing the pillar slipping behaviour—see below) at a velocity of 2.5 mm·s$^{-1}$. The XYZ-stage holds that position for 1.5 s, then moves laterally at a velocity of 2.5 mm·s$^{-1}$ for a total of 15 mm. The stage then moves vertically away from the prototype back to the starting height, thus unloading the forces, then moves laterally to return to the starting position.

By recording the XYZ-stage position that results in the desired normal force (5, 7.5, 10, 12.5, and 15 N), the spring constant can be calculated according to Hooke's Law. Since, at these normal force levels, all nine of the sensor pillars are compressed against the acrylic surface, the spring constant k is equal to ⅑th of the gradient of the line defined by stage position versus normal force.

To ensure that the three surfaces used for testing had different values of s and that the s of each surface remained consistent throughout the testing, it was necessary to measure the µs. The µs was measured by performing the protocol above at a normal force of 0.5 N—at this normal force, only the central pillar makes contact with the surface. The friction was measured before and after testing the pillar behaviour for each combination of frictional condition and testing normal force (see below).

The behaviour of the sensor was tested at five different normal force levels: 5, 7.5, 10, 12.5 and 15 N. The XYZ-stage was programmed to apply the normal and tangential forces as described above. At the same time, the force/torque signals from the ATI sensor were recorded and video was captured of the pillars in contact with acrylic surface.

Three surfaces were used with different frictional properties: (i) acrylic cleaned with ethanol (base friction condition), (ii) acrylic covered in olive oil (low friction condition), and (iii) acrylic coated with a thin layer of soap that has been allowed to dry (high friction condition).

For each combination of normal force (5, 7.5, 10, 12.5 and 15 N) and surface (acrylic: coated with oil, cleaned with alcohol, coated with soap), the following testing was performed: test friction at 0.5 N (once), test pillar behaviour at desired normal force (five times), test friction at 0.5 N (once).

To remove any high-frequency noise in the force signals, a 2nd-order low-pass Butterworth filter with a cut-off frequency of 10 Hz was applied.

The recorded videos were used to monitor the deflections of the central pillar and one of the eight outer pillars of the prototype during lateral movement of the acrylic surface. The Kanade-Lucas-Tomasi algorithm was used to perform point tracking in MATLAB (Mathworks, Natick, Mass., USA). Three points were tracked throughout the video recording: (i) the centre of the central pillar, (ii) the centre of one outer pillar—this was chosen as the pillar directly leading the central pillar in the direction of shearing—and (iii) a point on the reference grid (to monitor the position of the acrylic surface).

The result of point-tracking gives the deflection of the central and outer pillars relative to the position of the acrylic surface, and subsequently, relative to the undeflected position of each pillar. A single frame of the video tracking and the pillar deflection is shown in FIG. 4. A 5 Hz 2nd-order low-pass Butterworth filter was then applied to remove tracking jitter from the deflection data.

Synchronisation of the filtered force/torque and deflection signals were required since the original data were recorded on two different devices. At the end of each stimulus, the XYZ-stage accelerated in the negative Z-direction (normal to the pillars) to retract the acrylic surface away from the sensor, in order to unload the normal force. This results in a large acceleration in the measured normal force as well as the calculated central pillar deflection as the tangential bending force is suddenly removed. The large negative peaks in the second derivatives with respect to time of the filtered normal force and the central pillar deflection were used to synchronise the force and deflection data.

Ideally, since the stage is moving at a velocity of 2.5 mm·s$^{-1}$, if the pillar is stuck (not slipping), it too should be deflecting at a velocity of 2.5 mm·s$^{-1}$ at its tip, and when the pillar slips, the deflection velocity should become 0 mm·s$^{-1}$. This however is not the case in practice and due to bending of the pillar, the pillar first appears to move at the same velocity as the stage, however this velocity decreases slowly as the pillar appears to roll at the contact point. The moment of slip was therefore heuristically determined as the moment when the deflection velocity of the pillar (i.e., the first derivative of the deflection position with respect to time) decreased to 5% of the stage velocity (i.e. when the deflection velocity of the pillar first drops to below 0.125 mm·s$^{-1}$)—this is close to zero, but above the level of frame-to-frame noise of the pillar deflection velocity. In this work to prove the principle of operation of the prototype, this threshold was sufficient for identifying the moment of slip, however, in other real situations the detection algorithm will certainly need to be more complex/robust. In some forms, each protrusion may be instrumented internally using the light and pinhole method described above to measure its deflection and vibration of the protrusion. In some forms this may means the slip event will be less ambiguous.

The ratio of the tangential force to normal force at the moment of slip (as determined by the video analysis) of the central pillar (the only pillar in contact at 0.5 N of normal force) was taken to be an estimate of $\mu_s$.

The principle of operation of the sensor is that the outer (shorter) pillar should slip under a smaller tangential force compared to the central (taller) pillar. To determine whether this is satisfied, the tangential and normal forces at the moment of slip of the outer and central pillars respectively, were determined for comparison. A prediction of $\mu_s = F_T^{sC}/F_N^{sC}$ (Eq. (9)) was also calculated from the measured tangential and normal forces when the outer pillar slips ($F_T^{sO}$ and $F_N^{sO}$, respectively) and a comparison was made to the measured $F_T^{sC}/F_N^{sC}$ which are measured some time later when the central pillar finally slips.

Results

The stage positions (mm) for each of the normal forces (N) were used to calculate the spring constant, k, of the sensor pillars. The spring constant k, is the gradient of the line of best fit divided the number of pillars: k=1.174 N/mm.

It was observed that when the acrylic plate begins to shear (at approximately 2.4 s), there is a decrease in the normal force. This is expected as the XYZ-stage is programmed to remain at the same height while shearing the acrylic surface, and the pillars of the sensor bend, meaning that the effective height of the sensor decreases slightly. The $\mu_s$ was taken as the ratio of tangential force to normal force at the moment the central pillar slips.

Figure 7:
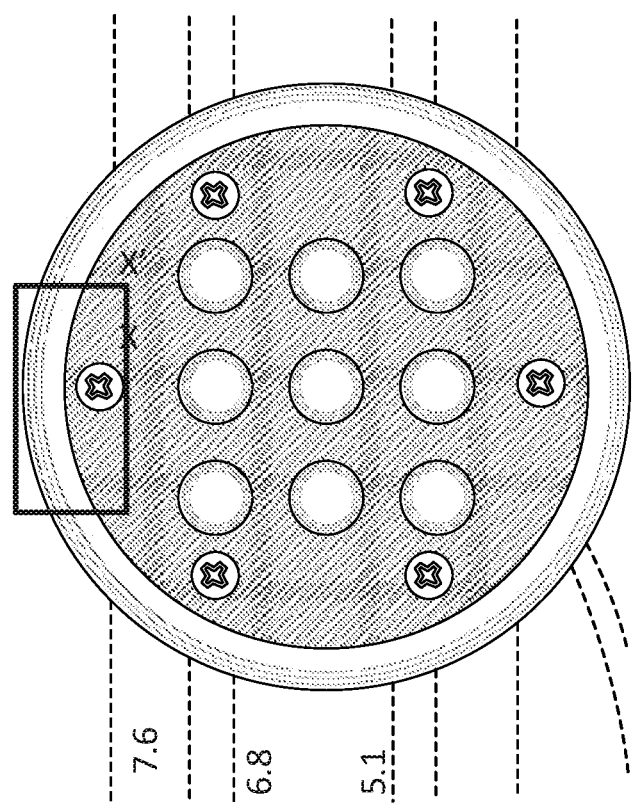
FIG. 7 shows a single frame of video captured during the testing procedure.

Referring to FIG. 7, shown is a single frame of video captured during the testing procedure. The red cross is the original position of the marker; the blue cross is the current position of the marker which moves with the acrylic plate. The values highlighted in yellow are the deflections (mm) of the marker (top), the central pillar (middle), and the outer pillar to the left of the central pillar (bottom).

Figure 8:
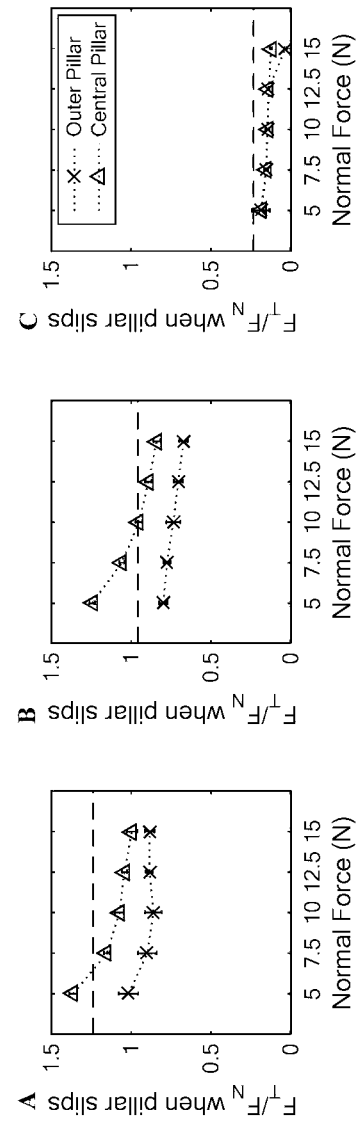
FIGS. 8A-8C provide a graphical view of tangential-to-normal force ratio at which each pillar slips at each normal force level.

Referring to FIG. 8, shown is a graphical view of tangential-to-normal force ratio at which each pillar slips at each normal force level for the A) high, B) base, and C) low friction surfaces. Markers are the mean values and error bars extend to ±SD. Dashed horizontal line indicates µs measured at 0.5 N normal force.

As shown in FIG. 9 A through 9C, the optical sensor is able to measure displacement of the protrusions and force on the protrusions. In the graphical representations, FIG. 9A provides reference displacement. The XY coordinates are obtained by tracking a dot which is stained on the tip of one pillar with a video camera from above. We bring a clear sheet of thick Perspex into contact with the pillar tip using a robotic stage and move it around to cause an XYZ displacement. The robotic stage tells us the Z coordinate.

FIG. 9C shows the reference force. This is obtained using a commercial 3-axis force sensor.

FIG. 9B shows measurement of the displacement and force using four photodiodes after some simple pre-processing. If there are four photodiodes arranged in a quadrant pattern as shown,

P Q
R S

Then the intensity of light they sense can be pre-processed as follows to get the middle plot.

$Z=P+Q+R+S$ (i.e., sum of all)

$X=[(P+R)-(Q+S)]/Z$ (i.e., left minus right, normalised)

$Y=[(P+Q)-(R+S)]/Z$ (i.e., top minus bottom, normalised)

Finally two mapping functions are learned to map the values measuring displacement and force shown in FIG. 9B to either: the values in FIG. 9A showing the reference displacement in three dimensions, or the values in FIG. 9C showing the reference forces in three dimensions.

Figure 10:
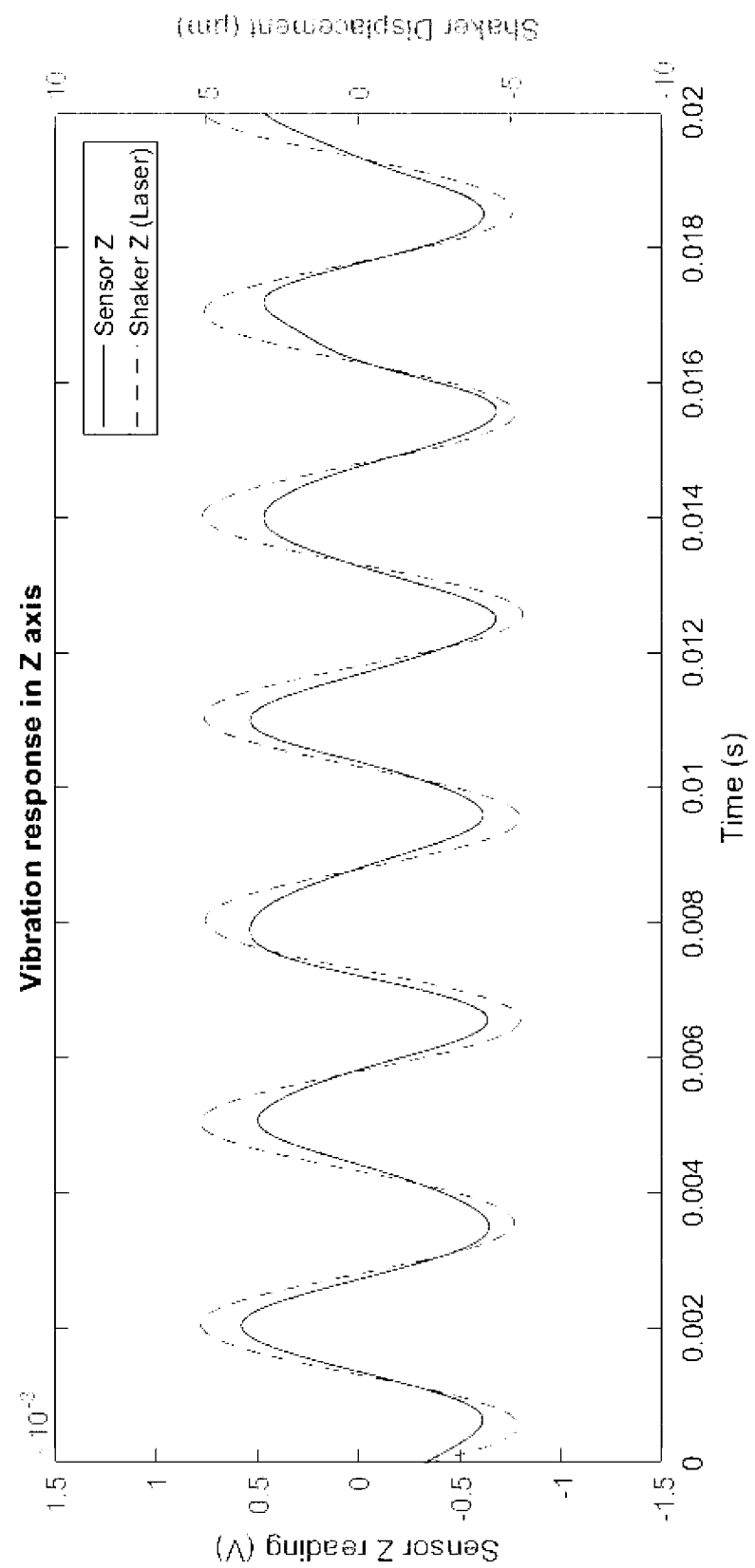
FIG. 10 shows detection of vibration response using an embodiment of the disclosure.

As shown in FIG. 10, the sensors can detect vibration. In this example the protrusion tip was in contact with a shaker which vibrates along a single axis. The attached image shows the results of a test where a 10 micron (0.01 mm) vibration at 330 Hz was applied in the Z axis of the pillar (i.e., compressing the pillar). The dotted red trace indicates the displacement of the shaker while the blue trace indicated the response of the photodiode sensor; this sensor response value shown in the blue trace was obtained using the calculation Z=P+Q+R+S, and is expressed in volts.

In the claims which follow and in the preceding description of the invention, except where the context requires otherwise due to express language or necessary implication, the word "comprise" or variations such as "comprises" or "comprising" is used in an inclusive sense; i.e., to specify the presence of the stated features but not to preclude the presence or addition of further features in various embodiments of the invention.

The invention claimed is:

1. A system for assessing grip security, the system comprising:
   a contact surface having at least a first contact surface region and a second contact surface region, the first contact surface region being configured to resist slip less than the second contact surface region,
   a sensor for detecting slip in the first contact surface region, wherein the contact surface comprises a plurality of protrusions extending from a base surface, the protrusions in the first contact surface region extending away from the base surface a distance less than the protrusions in the second contact surface region.

2. The system as claimed in claim 1, wherein the protrusions are deformable.

3. The system as claimed in claim 1, wherein protrusions are configured to move independently of one another.

4. The system as claimed in claim 1, wherein an uncompressed distance from the base surface of protrusions in the first contact region is less than that of protrusions in the second contact region.

5. The system as claimed in claim 1, wherein the protrusions are configured such that, in use under a consistent grip pressure, a normal force on a protrusion in the first contact region is less than that on a protrusion in the second contact region.

6. The system as claimed in claim 1, wherein the sensor is adapted to detect incipient slip.

7. The system as claimed in claim 1 wherein the protrusions each have an internal cavity, and wherein the sensor comprises a CCD array, the system being configured such that the CCD array detects light emanating from the base surface into the cavity, reflecting from a reflector located at a distal end of the cavity, and travelling through an aperture in the base surface to the sensor.

8. The system as claimed in claim 1, wherein the protrusions each have an internal cavity, and wherein the sensor comprises a CMOS light-sensitive array, the system being configured such that the CMOS light-sensitive array detects light emanating from the base surface into the cavity, reflecting from a reflector located at a distal end of the cavity, and travelling through an aperture in the base surface to the sensor.

9. The system as claimed in claim 1, wherein each protrusion comprises an internal cavity that extends from the base surface towards a distal end of the protrusion.

10. The system as claimed in claim 9, wherein a sensor is positioned behind the base surface at a location adjacent each cavity.

11. The system as claimed in claim 10, wherein an aperture having a smaller diameter than the cavity is located between the sensor and the cavity.

12. The system as claimed in claim 11, wherein the sensor comprises a quadrant photodiode configured to detect light emanating from LEDs positioned on a cavity side of the base surface within a given protrusion, reflecting from a reflector located at or near the distal end of the cavity and travelling through the aperture to the sensor.

13. A method for assessing grip security, the method comprising detecting slip at a contact surface, wherein the contact surface has at least a first contact surface region and a second contact surface region, the first contact surface region being configured to resist slip less than the second contact surface region,
wherein the contact surface comprises a plurality of protrusions extending from a base surface, the protrusions in the first contact region extending away from the base surface a distance less than the protrusions in the second contact region.

14. The method as claimed in claim 13, wherein the protrusions are positioned to extend from the base surface and form an array of protrusions.

15. The method as claimed in claim 13, wherein an uncompressed height from the base surface of a protrusion in the first contact region is shorter than that of a protrusion in the second contact region.

16. The method as claimed in claim 13, wherein the protrusions are configured such that a normal force experienced by a protrusion in the first contact region is less than that of a protrusion in the second contact region.

17. The method as claimed in claim 13, wherein each protrusion is associated with a sensor configured to detect light emanating from the base surface into a cavity, reflecting from a reflector located at a distal end of the cavity, and travelling through an aperture in the base surface to the sensor.

18. The method as claimed in claim 17, wherein the sensor comprises a means for detecting incipient slip.

19. The method as claimed in claim 17, wherein a rate at which slip events are detected by the sensor indicates when a corrective action is required or a magnitude of force required for a corrective action.

20. A method of estimating friction at a contact surface, the method comprising providing a plurality of protrusions extending from a base surface to a tip, measuring displacement of the tip in three dimensions using a sensor detecting light emanating from the base surface within a cavity of a given protrusion, reflecting from a reflector located at or near a distal end of the cavity, estimating forces applied to the tip in three dimensions at a moment of slip based on the displacement.

* * * * *